United States Patent [19]

Mita et al.

[11] Patent Number: 5,208,400
[45] Date of Patent: May 4, 1993

[54] PROCESS FOR PRODUCING ALLYL BROMIDES

[75] Inventors: Ryuichi Mita; Yuji Fukunaga; Hironobu Horie; Mitsumasa Umemoto; Yasuhiro Matsuki, all of Ohmuta, Japan

[73] Assignee: Mitsui Toatsu Chemicals, Inc., Japan

[21] Appl. No.: 815,778

[22] Filed: Jan. 2, 1992

Related U.S. Application Data

[63] Continuation of Ser. No. 534,228, Jun. 7, 1990, abandoned.

[30] Foreign Application Priority Data

| | | | |
|---|---|---|---|
| Jun. 14, 1989 | [JP] | Japan | 1-149513 |
| Jul. 4, 1989 | [JP] | Japan | 1-171213 |
| Jul. 28, 1989 | [JP] | Japan | 1-194247 |

[51] Int. Cl.$^5$ .............................................. C07C 17/20
[52] U.S. Cl. .................................................... 570/235
[58] Field of Search ......................................... 570/235

[56] References Cited

U.S. PATENT DOCUMENTS 3,406,215 10/1968 Holmquist .

FOREIGN PATENT DOCUMENTS 925147 5/1963 United Kingdom .

OTHER PUBLICATIONS

Quartulli, Hydrocarbon Processing, Oct. 1975, pp. 94-99.

*Primary Examiner*—Howard T. Mars
*Attorney, Agent, or Firm*—Millen, White, Zelano & Branigan

[57] ABSTRACT

An improved process for producing allyl bromides by halogen exchange by reaction of an allyl chloride, with a metal bromide, wherein the reaction is conducted in an aprotic polar solvent. The allyl bromides obtained by the process of the invention are useful as intermediates for producing medicines, agricultural chemicals, dyes, and the like.

8 Claims, No Drawings

PROCESS FOR PRODUCING ALLYL BROMIDES

This is a continuation of application Ser. No. 07/534,228 filed Jun. 7, 1990, now abandoned.

BACKGROUND OF THE INVENTION

1. Field of the Invention

The present invention relates to an improved process for producing allyl bromides useful in the field of synthetic organic chemistry, in particular, as intermediates for producing fine chemical products, such as agricultural chemicals, medicines, dyes, etc.

2. Description of the Prior Art

Various processes have hitherto been disclosed with regard to the production of allyl bromides represented by Formula (I) of the following:

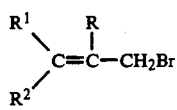
(I)

(wherein R, $R^1$ and $R^2$ each independently represents a hydrogen atom or a lower alkyl group).

Of allyl bromides represented by Formula (I), allyl bromide ($R^1=R^2=H$), the basic compound represented by the formula, is generally produced by reacting allyl alcohol with hydrobromic acid in the presence of sulfuric acid. In Organic Synthesis, Coll. Vol. 1, p.27 (1967), for example, 5.9 mol of 48% hydrobromic acid is admixed with 4 mol of allyl alcohol, and 300 g of concentrated sulfuric acid is gradually added with stirring to the mixture, followed by the distillation thereof to obtain allyl bromide. By this method, the desired allyl bromide can be produced almost quantitatively in a yield of 92 to 96%. However, the method is disadvantageous as an industrial process since it utilizes a large quantity of sulfuric acid and hence results in the generation of a large quantity of waste which must be subjected to costly treatments, including neutralization.

There is also known a process in which propylene is brominated with hydrogen bromide at an elevated temperature (350° to 450° C.) in the presence of a pearlite catalyst to produce allyl bromide [Soviet Patent No. 753,841 (1980)]. In this process, however, 1-bromopropene is produced as a by-product, and allyl bromide is formed with only a low selectivity. In addition, the by-product could not be separated without difficulty.

It is also known that allyl bromides can be produced from allyl chlorides through halogen exchange. For example, in Journal of the Organic Chemistry USSR, Vol. 10, p. 1,122 (1974), allyl chloride or methallyl chloride is subjected to halogen exchange with an excess of hydrobromic acid in the presence of cuprous chloride to produce allyl bromide or methallyl bromide.

In Journal of the American Chemical Society, Vol. 72, p. 4,316 (1950) is disclosed a process in which methallyl chloride is subjected to halogen exchange with sodium bromide in methanol to give methallyl bromide, as well as a process in which methallyl chloride is treated with lithium bromide in acetone to give methallyl bromide.

In the former process, however, methallyl chloride can be converted at a conversion rate of only 70% or less, and the catalyst used contains heavy metals which have been placed under severe industrial regulation and hence requires a particular caution for the treatment of waste water contaminated with them. In the latter process, the halogen exchange in methanol gives methallyl bromide in only an extremely low yield due to the formation of large quantities of by-products, such as methallyl methyl ether, etc., and the halogen exchange in acetone gives methallyl bromide in a yield of only 54% at best.

Although a number of other processes are known for the production of allyl bromides, they are not satisfactory in yield, materials employed, and the like.

It is therefore the present state of the art that none of the hitherto known processes for producing allyl bromides is satisfactory in overall with regard to yield, process, conditions, and the like.

Taking into consideration the present state of the art described hereinabove, the present inventors have conducted intensive investigations to establish an effective, commercially advantageous process for producing allyl bromides from allyl chlorides.

It is known that the exchange of halogen between halogenated alkyls is in general an equilibrium reaction. The conversion of allyl chlorides into allyl bromides according to the present invention is also an equilibrium reaction. It is therefore theoretically possible to continuously draw the reaction product (allyl bromides) out of the reaction system, or to use the halogen exchanging agent (allyl chlorides) in large excess, so as to allow the conversion to proceed in a favorable manner. However, when the former technique is applied to the conversion, it can be extremely difficult to selectively separate allyl bromides alone during the course of the reaction since both the raw material (allyl chlorides) and the product (allyl bromides) are liquid and are highly soluble in ordinary organic solvents and, in addition, they have similar physical properties. The latter technique has a difficulty in dissolving metal bromides in large quantities, in the recovery and recycling of metal bromides, and in the separation of metal chlorides generated as by-products.

SUMMARY OF THE INVENTION

The present invention relates to an improved, highly efficient process for producing allyl bromides, e.g., those represented by Formula (I):

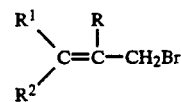
(I)

wherein R, $R^1$ and $R^2$ each independently represents a hydrogen atom or a lower alkyl group from the corresponding allyl chlorides, e.g., those represented by Formula (II):

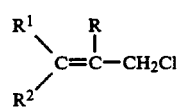
(II)

wherein R, $R^1$ and $R^2$ have the same meanings as above by a halogen exchange reaction with a metal bromide in an aprotic polar solvent.

DETAILED DESCRIPTION OF THE INVENTION

The process of the present invention will further be explained hereinbelow.

The present inventors have carried out studies in search of a method for effectively converting allyl chlorides into allyl bromides by using metal bromides in relatively small quantities. As a result, it has now been found that certain solvents, for example, N,N-dimethylformamide, N,N'-dimethylimidazolidinone, etc., are a good solvent for metal bromides but a poor solvent for the corresponding metal chlorides, and that when the halogen exchange is carried out in one of such solvents, the desired reaction proceeds under mild conditions without requiring a co-catalyst, thereby producing the corresponding allyl bromide in high yield, and that after separated from the allyl bromide formed and any unreacted allyl chloride therefrom by distillation, the reaction solvent can be recycled into the reaction system without any further purification.

For example, where allyl bromide is produced from allyl chloride, using N,N-dimethylformamide as the solvent and 1.2 moles of sodium bromide as a halogen exchanging agent per mole of allyl chloride, the reaction proceeds smoothly at 40° C. to give the desired allyl bromide in a yield of about 90%, forming no substantial by-products. After the sodium chloride is filtered off and the unreacted allyl chloride and the desired allyl bromide are removed by distillation, the N,N-dimethylformamide which remains as a still residue can be used again in the halogen exchange reaction without further purification and gives reaction results not significantly different from those wherein fresh N,N-dimethylformamide is employed.

In accordance with the process of the present invention, allyl chlorides can be converted into corresponding allyl bromides in high yields even under mild conditions, without using metal bromides (halogen exchanging agent) in large molar excess. In addition, allyl bromides formed can be easily isolated since it is possible to employ a solvent having a boiling point which differs substantially from that of the product.

Furthermore, the process of the present invention has important commercial significance since it has the advantage that the aprotic polar solvent used can be recycled with no further purification after the allyl bromide formed is removed by distillation.

In Table 1 is shown the solubility of sodium chloride and sodium bromide in N,N-dimethylformamide and N,N'-dimethylimidazolidinone.

TABLE 1

| Solubility of Sodium Bromide and Sodium Chloride | | | | | |
| --- | --- | --- | --- | --- | --- |
| | | N,N-dimethylformamide | | N,N'-dimethylimidazolidine | |
| | | 25° C. | 55° C. | 25° C. | 55° C. |
| Solubility (Wt %) | NaBr | 10.1 | 8.1 | 5.8 | 5.3 |
| | NaCl | 0.05 | 0.03 | 0.04 | 0.03 |

The present invention has been accomplished on the basis of the above finding and the results of the above studies.

In the present invention, allyl chlorides represented by Formula (II) are used as a raw material. As specific examples of usable allyl chlorides, mention may be made of allyl chloride, methallyl chloride, γ-methylallyl chloride, γ,γ-dimethylallyl chloride, β-methyl-γ,γ-dimethylallyl chloride, γ-ethylallyl chloride, γ-n-propylallyl chloride, γ-isopropylallyl chloride, γ-n-butylallyl chloride, γ-sec-butylallyl chloride, γ-isobutylallyl chloride, γ-tert-butylallyl chloride, and the like.

In the present invention, metal bromides are used as an agent for exchanging halogen with allyl chlorides represented by Formula (II). There is no particular restriction on the kind of metal bromides to be used, provided that they are readily soluble in an aprotic polar solvent and their corresponding metal chlorides are hardly soluble therein. In most cases, it can be advantageous from economical point of view to use sodium bromide or potassium bromide. These metal bromides are usually used individually. It is however however possible to use two or more metal bromides in combination.

The reaction can be conducted using 1.0 to 3.0 moles of metal bromide, per mole of allyl chloride, although it can proceed even when metal bromides are used in a quantity less than stoichiometrically required. In usual cases, however, metal bromides are used in an amount greater than stoichiometrically required, taking into consideration the conversion rate of the raw material (allyl chlorides) and the yield of the desired product (allyl bromides). Although there is no particular upper limit on the amount of metal bromides to be used, it can be preferable from economical point of view to use metal bromides in an amount not greater than 3 moles, per mole of allyl chlorides.

A characteristic feature of the present invention is that the halogen exchange reaction of allyl chlorides is carried out in an aprotic polar solvent. The aprotic polar solvent not only functions as a good solvent for metal bromides, but allows the halogen exchange reaction to proceed smoothly under mild conditions.

As specific examples of aprotic polar solvents usable in the present invention, mention may be made of N,N-dimethylformamide, N,N-diethylformamide, N,N-dimethylacetamide, N,N-diethylacetamide, N-methylpyrrolidone, N-ethylpyrrolidone, N,N'-dimethylimidazolidinone, N,N'-dimethylpropyleneurea, dimethylsulfoxide, sulfolane, hexamethylphosphoramide, and the like. Of these solvents, N,N-dimethylformamide, N,N-dimethylacetamide, N,N-diethylacetamide, N,N'-dimethylimidazolidinone and N,N'-dimethylpropyleneurea can be preferable. When the halogen exchange reaction of the present invention is carried out in such a solvent, the conversion of allyl chlorides into allyl bromides proceeds smoothly even under highly mild conditions, with formation of almost no by-products. Accordingly, allyl bromides can be formed in high yields with almost perfect selectivity. In addition, the products can be isolated quite easily since the difference between the boiling point of such a solvent and that of allyl bromides is large. Moreover, such a solvent, after allyl bromides have been isolated by means of distillation, can be recycled without being subjected to any purification.

The aprotic polar solvents are usually used individually. It is however possible to use two or more kinds of aprotic polar solvents simultaneously. In usual cases, these solvents are used in a state substantially free from water. It is however permissible to use a solvent which contains water in an amount not causing adverse effects against the halogen exchange according to the present invention.

The aprotic polar solvents are used in a quantity sufficient to dissolve the metal bromide. If the metal bromide is dissolved only partially, this results in an extremely slow halogen exchange reaction between the allyl chloride and the metal allyl bromide. Accordingly, aprotic polar solvents are used ordinarily in an amount not less than 0.3 times (based on weight), preferably not less than 0.5 times, that of allyl chlorides. Although there is no particular upper limit on the quantity of aprotic polar solvents used, it is however not preferable with respect to volume efficiency to use the solvents in a large excess. Accoringly, the solvents are ordinarily used in an amount up to 10 times the weight of allyl chlorides.

Specific embodiments for practicing the process of the present invention are as follows:

A predetermined quantity of sodium bromide is added to N,N-dimethylformamide containing dissolved therein 1 mol of allyl chloride, and the reaction is allowed to proceed with stirring at a temperature in the range of from 0° to 150° C., preferably from the room temperature e.g., 20° C. to 100° C. The order of mixing of the raw materials and the solvents is not critical. It is therefore possible to add allyl chlorides to a solution containing metal bromides dissolved or suspended therein. The reaction can be carried out in various manners. For example, it can be allowed to proceed after the entire solvent and raw materials have been charged. It is also possible to add allyl chlorides dropwise or to charge metal bromides by portions to allow the reaction to proceed.

In the present invention, the progress of the reaction can be determined by means, e.g., of gas chromatography.

The allyl bromide formed by the above halogen exchange is then subjected to an isolation step, e.g., by subjecting the reaction mixture to distillation after the metal chloride contained therein have been removed by subjecting the mixture to a solid-liquid separating operation, if necessary, after cooling. Alternatively, the reaction mixture can be subjected directly to distillation to isolate the allyl bromide and any unreacted allyl chloride. As examples of appropriate solid-liquid separating operations, mention may be made of natural filtration, suction filtration, pressure filtration, decantation, centrifugation, and the like. The distillation of the allyl bromide can be carried out either at ordinary pressure or at reduced pressure. Allyl bromides can readily be isolated by distillation, with no substantial decomposition thereof.

In the case where the reaction mixture is directly subjected to distillation to isolate allyl bromides, the still residue, which remains in the distillation still after allyl bromides have been distilled off, may be subjected to cooling to deposit the metal chloride, which can be removed by means of a solid-liquid separating operation.

As described above, aprotic polar solvents used in the present process can be recovered in accordance with the following steps: Halogen exchange reaction→isolation of metal chloride→isolation (distillation) of allyl bromide; or halogen exchange reaction→isolation of allyl bromide→separation of metal chloride. Aprotic polar solvents so recovered contain a substantial portion of unreacted metal bromide, although the quantity of unreacted metal bromide dissolved therein varies depending on the quantity of solvent used, the quantity of metal bromide used, the order of the post reaction treatments, etc. The solvents can be returned to the reaction system without being subjected to any purification since no substantial by-products other than metal chloride are formed in the course of the reaction and post reaction treatments. Upon recycling of the solvent so recovered, the quantity of fresh metal bromide supplemented thereto can be reduced accordingly, taking into consideration the quantity of unreacted metal bromide contained therein. There is no substantial restriction on the number of times the recovered solvent can be recycled.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above and below, are hereby incorporated by reference.

EXAMPLE 1

(Synthesis of Allyl Bromide)

Into a four-necked flask were charged 38.3 g (0.5 mol) of allyl chloride, 61.7 g (0.6 mol) of sodium bromide and 76.6 g of N,N-dimethylformamide. While stirring, the temperature of the mixture was raised to 40° C., and the reaction was allowed to proceed at 40° to 45° C. for 10 hours. After the completion of the reaction, part of the resulting reaction mixture was analyzed by gas chromatography. The yield of allyl bromide was 90.3%, based on the allyl chloride charged, and the remaining rate of allyl chloride was 9.1%, based on the allyl chloride charged.

Allyl bromide formed was isolated as follows: The reaction mixture was cooled to room temperature, and then sodium chloride deposited was filtered off with suction and washed with N,N-dimethylformamide. The filtrate and the washings were combined and distilled at ordinary pressure in a distillation apparatus equipped with a fractionating column to give 51.8 g of allyl bromide having a purity of 98% or above (b.P.: 69.5° to 71.0° C.). The yield of allyl bromide was 85.6%, based on the allyl chloride. There was obtained as an initial distillate 6.4 g of mixture of allyl chloride and allyl bromide.

EXAMPLES 2 TO 5

The procedure of Example 1 was repeated, using different kinds of halogen exchanging agents and reaction media in different quantities under different reaction conditions. Results obtained are shown in Table 2.

COMPARATIVE EXAMPLE 1

(Synthesis of Allyl Bromide in Methanol)

Into a four-necked flask were charged 38.3 g (0.5 mol) of allyl chloride, 61.7 g of sodium bromide and 76.6 g of methanol. While being stirred, the mixture was heated under reflux for 10 hours. After being cooled to room temperature, part of the resulting reaction mixture was analyzed by gas chromatography. The yield of allyl bromide was 18.6%, based on the allyl chloride charged.

EXAMPLE 6

(Synthesis of Allyl Bromide With Recycling of Solvent)

The procedure of Example 1 was repeated, and 80 g of the still residue remained after allyl bromide had been distilled off was charged into a four-necked flask without any purification. Into the same flask were additionally charged 38.3 g (0.5 mol) of allyl chloride and 56.7 g (0.55 mol) of sodium bromide. While stirring, the temperature of the mixture was raised to 40° C., and the reaction was allowed to proceed at 40° to 45° C. for 10 hours. After the completion of the reaction, part of the resulting reaction mixture was analyzed by gas chromatography. The yield of allyl bromide was 89.5%.

The reaction mixture was subjected to the same post treatment and distillation as in Example 1 to give 50.9 g of allyl bromide. Yield: 84.1% (based on the allyl chloride).

EXAMPLES 7 TO 9

Various allyl bromides were synthesized in a similar manner as in Example 1, using different kinds of allyl chlorides. Results obtained are shown in Table 3.

EXAMPLE 10

Into a four-necked 500 ml flask were placed charged 90.5 g (1.0 mol) of methallyl chloride and 181 g of N,N-dimethylformamide. After 123.6 g (1.2 mol) of sodium bromide had been additionally charged thereinto, the reaction was allowed to proceed with stirring at 40° C. for 20 hours. After the completion of the reaction, part of the liquid portion of the resulting reaction mixture was analyzed by gas chromatography. The yield was methallyl bromide was 91.8%, based on the methallyl chloride charged. It was found that the percentage of unreacted methallyl chloride was 7.6%, based on the methallyl chloride charged, and that methallyl bromide was formed highly selectively with almost no substantial formation of by-products.

After the reaction, the product was isolated as follows: The reaction mixture was cooled to room temperature, and then sodium chloride deposited was filtered off with suction and washed with a small quantity of N,N-dimethylformamide. The filtrate and the washings were combined and distilled under reduced pressure by using a fractionator to give 116.4 g of methallyl bromide of a boiling point of 52.0° to 53.0° C./200 mm Hg. Purity: 98% or above. Yield: 85.6% (based on the methally chloride).

There was obtained as an initial distillate 13.7 g of mixture of methallyl chloride and methallyl bromide.

EXAMPLE 11

The procedure of Example 10 was repeated, except that 181 g of N,N'-dimethylimidazolidinone was used instead of N,N-dimethylformamide and the reaction was allowed to proceed at 60° C. for 10 hours. After the reaction, part of the liquid portion of the resulting reaction mixture was sampled and analyzed by gas chromatography. The yield of methallyl bromide was 90.2%, based on the methallyl chloride.

EXAMPLE 12

The procedure of Example 10 was repeated, except that 178.7 g (1.5 mol) of potassium bromide was used instead of sodium bromide, and the resulting reaction mixture was analyzed by gas chromatography. The yield of methallyl bromide was 94.1%, based on the methallyl chloride.

EXAMPLES 13 TO 18

Methallyl bromide was synthesized from 27.2 g (0.3 mol) of methallyl chloride, using sodium bromide or potassium bromide (halogen exchanging agent) in combination with various aprotic polar solvents in quantities shown in Table 4. Results obtained are shown in the table.

EXAMPLE 19

Into a four-necked 500 ml flask were placed 90.5 g (1.0 mol) of methallyl chloride and 181 g of N,N-dimethylformamide. After 123.6 g (1.2 mol) of sodium bromide had been additionally added thereto, the reaction was allowed to proceed with stirring at 40° C. for 20 hours. After the reaction, part of the solution was sampled and analyzed by gas chromatography. The yield of methallyl bromide was 91.8%, based on the methallyl chloride.

The percentage of unreacted methallyl chloride was 7.6%, based on the methallyl chloride charged, and methallyl bromide was formed highly selectively with no substantial formation of by-products.

Subsequently, the reaction mixture was cooled to room temperature, and sodium chloride deposited was filtered off and washed with a small quantity of N,N-dimethylformamide. The filtrate and the washings were combined and distilled under reduced pressure by using a fractionator to give 116.4 g of methallyl bromide of a boiling point of 52.0° to 53.0° C./200 mmHg. Purity: 98% or above. Yield: 85.6% (based on methallyl chloride).

There was obtained as an initial distillate 17.3 g of mixture of methallyl chloride and methallyl bromide.

EXAMPLE 20

(Recycling of Solvent)

The halogen exchange reaction was carried out in the same manner as in Example 1, except that N,N-dimethylformamide remained as a still residue after the distillation of methallyl bromide in Example 19 was used as reaction medium. After the reaction, part of the reaction mixture was sampled and analyzed by gas chromatography. The yield of methallyl bromide was 90.2%, based on the methallyl chloride.

After the reaction, the reaction mixture was treated in the same manner as in Example 18 to give 113.3 g of methallyl bromide. Yield: 83.9% (based on the methallyl chloride).

The solvent recovered during the above post treatment was recycled once again under the same reaction conditions. There was obtained methallyl bromide in a yield of 90.8%.

EXAMPLE 21

Into a four-necked 500 ml flask were placed 90.5 g (1.0 mol) of methallyl chloride and 181 g of N,N'-dimethylimidazolidinone. After 154.4 g (1.5 mol) of sodium bromide was additionally charged thereinto, the reaction was allowed to proceed with stirring at 60° C. for 10 hours. After the reaction, part of the reaction mixture was sampled and analyzed by gas chromatography. The yield of methallyl bromide was 91.3%, based on the methallyl chloride. Subsequently, the reaction mixture was directly subjected to distillation under reduced pressure using a fractionator to give 114.8 g of methallyl bromide of a boiling point of 52.0 to 53.0° C./200 mmHg. Purity: 98% or above. Yield: 85.0% (based on the methallyl chloride).

After methallyl bromide had been isolated by distillation, the still residue was cooled to room temperature, and sodium chloride deposited was filtered off and washed with a small quantity of N,N'-dimethylimidazolidinone. The filtrate and the washings were combined and used again in the subsequent reaction.

To 190 g of the combined filtrate and washings, which contained 9 g of sodium bromide, were added 90.5 g (1.0 mol) of methallyl chloride and 145.4 g (1.41 mol) of fresh sodium bromide, and the reaction was allowed to proceed at 60° C. for 10 hours. After the reaction, part of the reaction mixture was sampled and analyzed by gas chromatography. The yield of methallyl bromide was 90.3%.

Subsequently, the reaction mixture was distilled at a pressure of 200 mmHg to give 112.7 g of methallyl bromide.

EXAMPLES 22 to 24

The procedure of Example 19 was repeated, using solvents and metal bromides shown in Table 5. Subsequently, the same reactions were carried out under the same conditions, except that solvents which had been recovered as still residues after the distillation of metal bromide were used as reaction media. Results obtained are shown in Table 5.

TABLE 2

| | Solvent Used | | Synthesis of Allyl Bromide* Metal Bromide Used | | Reaction Conditions | Yield of Allyl |
|---|---|---|---|---|---|---|
| | Kind | (g) | Kind | Amount** | (°C./Hr) | Bromide (%)*** |
| Example 2 | Dimethylsulfoxide | 76.6 | Potassium bromide | 1.2 | 40/10 | 88.7 |
| Example 3 | N,N'-dimethyl-imidazolidinone | 38.3 | Sodium Bromide | 1.5 | 50/10 | 87.4 |
| Example 4 | N,N-dimethylacetamide | 76.6 | Sodium Bromide | 1.2 | 60/8 | 90.5 |
| Example 5 | Sulfolane | 76.6 | Sodium Bromide | 1.2 | 40/10 | 90.1 |

[Notes]
*Allyl chloride was used in an amount of 38.3 g (0.5 mol scale).
**Shown in moles of metal bromide used per mole of allyl chloride.
***Based on allyl chloride used (determined by gas chromatography).

TABLE 3

| | Synthesis of Various Allyl Bromides* | | | | | | |
|---|---|---|---|---|---|---|---|
| | Allyl Chlorides Used | | | Solvent Used | | Allyl Bromides** | |
| | Kind | (g) | (mol) | Kind | (g) | Product | Yield*** |
| Example 7 | $CH_3CH=CHCH_2Cl$ | 45.3 | 0.5 | N,N-dimethylformamide | 91 | $CH_3CH=CHCH_2Br$ | 91.3% |
| Example 8 | $C_2H_5CH=CHCH_2Cl$ | 52.3 | 0.5 | N,N'-dimethylimidazolidinone | 105 | $C_2H_5CH=CHCH_2Br$ | 90.6% |
| Example 9 | $(CH_3)_2C=CHCH_2Cl$ | 52.3 | 0.5 | N,N'-dimethylimidazolidinone | 105 | $(CH_3)_2C=CHCH_2Br$ | 90.1% |

[Notes]
*Sodium bromide was used in an amount of 77.3 g (1.5 mol/per mol of allyl chloride), and the reactions were conducted at 40° C. for 10 hours.
**Part of the reaction mixture was analyzed by gas chromatography.
***Based on allyl chloride used.

TABLE 4

| | Reaction Media Used | | Metal Bromide Used | | Reaction Conditions | Yield of Metallyl |
|---|---|---|---|---|---|---|
| | Kind | Amount* | Kind | Amount** | Temp. (°C.)/Hrs. | Bromide*** |
| Example 12 | N,N-dimethylformamide | 1.0 | Sodium bromide | 1.0 | 40/20 | 85.9 mol % |
| Example 13 | N,N'-dimethylimidazolidinone | 0.5 | Sodium bromide | 1.0 | 40/20 | 80.5 mol % |
| Example 14 | N,N'-dimethylimidazolidinone | 3.0 | Sodium bromide | 2.0 | 40/20 | 88.6 mol % |
| Example 15 | N,N-dimethylacetamide | 2.0 | Potassium bromide | 1.5 | 60/10 | 90.9 mol % |
| Example 16 | N-methylpyrrolidone | 2.0 | Sodium bromide | 1.5 | 30/20 | 89.4 mol % |
| Example 17 | Dimethylsulfoxide | 2.0 | Sodium bromide | 1.5 | 40/10 | 88.1 mol % |

[Notes]
*Times in weight, based on the weight of methallyl chloride used.
**Moles, per mol of methallyl chloride used.
***Based on the mol of methallyl chloride used.

TABLE 5

Synthesis of Methallyl Bromide*

| | Reaction Media Used | | Metal Bromide Used | | Yield of Methallyl Bromide** | |
|---|---|---|---|---|---|---|
| | Kind | (g) | Kind | Amount*** | A**** | B***** |
| Example 22 | N,N-dimethylacetamide | 181 | Potassium bromide | 1.5 | 90.6% | 89.4% |
| Example 23 | Dimethylsulfoxide | 181 | Sodium bromide | 1.5 | 88.1% | 88.3% |
| Example 24 | N-methylpyrrolidone | 181 | Sodium bromide | 1.5 | 89.2% | 88.9% |

[Notes]
*Methallyl chloride was used in an amount of 90.5 g (1.0 mol scale), and the reactions were conducted at 40° C. for 20 hours.
**Based on methallyl chloride used.
***Moles, per mole of methallyl chloride used.
****Results obtained when fresh solvents were used.
*****Results obtained when recycled solvents were used.

What is claimed is:

1. In a process for preparing an allyl bromide represented by the formula (I):

wherein R represents a hydrogen atom or a methyl group, by a halogen exchange reaction of an allyl chloride represented by the formula (II) with a metal bromide in a reaction solvent,

wherein R is defined as in the formula (I),
the improvement which comprises recycling the reaction solvent without the necessity of its purification by carrying out the halogen exchange reaction in an aprotic polar solvent and thereafter employing the following steps (a) or (b):
(a) (1) first removing the formed metal chloride as a solid from the reaction product,
(2) then separating the unreacted allyl chloride and the formed allyl bromide from the reaction product by distillation, and
(3) then recycling, without purification, the aprotic polar solvent remaining as a distillation residue; or
(b) (1) first separating the unreacted allyl chloride and the formed allyl bromide by distillation,
(2) cooling the thus formed distillation residue,
(3) then removing the formed metal chloride as a solid from the liquid phase of the distillation residue, and
(4) then recycling, without purification, the aprotic polar solvent recovered as the liquid phase of the distillation residue.

2. The process of claim 1, wherein the aprotic polar solvent is at least one member of the group consisting of N,N-dimethylformamide, N,N-diethylformamide, N,N-dimethylacetamide, N,N-diethylacetamide, N-methylpyrrolidone, N-ethylpyrrolidone, N,N-dimethylimidazolidinone, N,N'-dimethylpropyleneurea, dimethylsulfoxide, sulfolane and hexamethylphosphoramide.

3. The process of claim 1, wherein the aprotic polar solvent is at least one member of the group consisting of N,N-dimethylformamide, N,N-dimethylacetamide, N,N-diethylacetamide, N,N-dimethylimidazolidinone and N,N'-dimethylpropyleneurea.

4. The process of claim 1, wherein the allyl chloride is methallyl chloride.

5. The process of claim 1, wherein the metal bromide is one or both of sodium bromide and potassium bromide.

6. The process of claim 1, wherein the metal bromide is used in an amount of 1.0 to 3.0 moles, per mole of allyl chloride.

7. The process of claim 1, wherein the halogen exchange reaction is conducted at a temperature of 40° to 60° C.

8. The process of claim 3, wherein the allyl chloride is methallyl chloride; wherein the metal bromide is one or both of sodium bromide and potassium bromide; and wherein the metal bromide is used in an amount of 1.0 to 3.0 moles, per mole of allyl chloride.

* * * * *